United States Patent [19]

Deckers et al.

[11] Patent Number: 5,512,556
[45] Date of Patent: Apr. 30, 1996

[54] USE OF A PREGNANE DERIVATIVE

[75] Inventors: Godefridus H. J. Deckers, HW Oss; Helenius J. Kloosterboer, AV Oss, both of Netherlands

[73] Assignee: Akzo Nobel N.V., Arnhem, Netherlands

[21] Appl. No.: 358,639

[22] Filed: Dec. 19, 1994

Related U.S. Application Data

[63] Continuation of Ser. No. 206,994, Mar. 7, 1994, abandoned.

[30] Foreign Application Priority Data

Mar. 5, 1993 [EP] European Pat. Off. ............. 93200631

[51] Int. Cl.$^6$ .................................................. A61K 31/56
[52] U.S. Cl. ........................ 514/177; 514/169; 514/182
[58] Field of Search ................................. 514/169, 177, 514/182

[56] References Cited

FOREIGN PATENT DOCUMENTS

| 0159739 | 10/1985 | European Pat. Off. ............. 514/177 |
|---|---|---|
| 0389035 | 9/1990 | European Pat. Off. ............. 514/177 |

OTHER PUBLICATIONS

R. Smith et al., "Hormone Replacement Therapy: A Review", *Journal of Drug Development*, vol 4, No. 4, pp. 235–344, 1992.

L. Markiewicz et al., "In Vitro Evaluation of Estrogenic, Estrogen Antagonistic and Progestagenic Effects of a Steroidal Drug (Org OD–14) and its Metabolites on Human Endometrium" *The Journal of Steroid Biochemistry* vol. 35, No. 5, Apr. 1990, pp. 535–541.

*Primary Examiner*—Jerome D. Goldberg
*Attorney, Agent, or Firm*—Mary E. Gormley

[57] ABSTRACT

The invention relates to a use of pregnane derivatives of the following general formula:

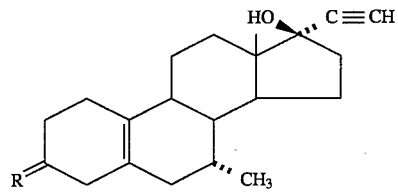

in which R=$H_2$, (H,OH), (H,OAcyl), or O, and especially the pregnane derivative(7α,17α)-17-hydroxy-7-methyl-19-nor-17-pregn-5(10)-en-20-yn-3-one (compound I), for the manufacture of a medicament for the prevention or treatment of tumors.

5 Claims, No Drawings

USE OF A PREGNANE DERIVATIVE

This is a continuation of application Ser. No. 08/206,994 filed Mar. 7, 1994, now abandoned.

FIELD OF THE INVENTION

The invention relates to the use of pregnane derivatives for the manufacture of a medicament for the prevention or treatment of tumors.

BACKGROUND OF THE INVENTION

In the endocrine therapy of breast cancer, patients may be treated with hormones, like progestogens (G. H. Bakker et al. in Hormonal Manipulation of Cancer: Peptides, Growth Factors, and New (Anti) Steroidal Agents, edited by Jan G. M. Klijn et al., Raven Press, New York, 1987, p. 39) and androgens (M. N. Teller et al., Cancer Res. 26, No.2, Pt.1, 245, 1966; S. Dauvois et al., Ann. N.Y.Acad.Sc. 595, 413, 1990). Cancer treatment with progestogens gives, however, undesirable side-effects, especially when applied in high dosages, such as abdominal distension and pain, nausea, headache, depression, and the like. When androgens are applied, also a number of unfavourable side-effects occurs, of which virilizing phenomena like hoarseness, hirsutism and alopecia are most frequently observed.

The use of other drugs not having the above-mentioned undesired side-effects would be highly favorable. However, it is known that such drugs are not permitted to have estrogen activity: drugs with estrogen activity cannot be used in patients having breast cancer due to the apparent estrogen sensitivity of mammary tumors (R. W. Brueggemeier et al., Cancer Research 48 6808, 1988; Y. J. Abul-Hajj, J. Steroid Biochem., 34, 439, 1989).

SUMMARY OF THE INVENTION

We now have found compounds which are suitable for preventing or treating cancer, in particular mammary tumors, with improved properties with respect to side-effects.

DETAILED DESCRIPTION OF THE INVENTION

The invention relates to the use of pregnane derivatives of the following general formula:

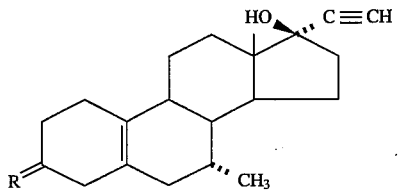

in which R=$H_2$, (H,OH), (H,OAcyl), or O, for the preparation of a medicament for the prevention or treatment of tumors. These compounds, in particular the derivatives in which R=(H,OH) or O, and especially the pregnane derivative in which R=O (7α, 17α)-17-hydroxy7-methyl-19-nor-17-pregn-5(10)-en-20-yn-3-one (compound I), have in rats a clearly established estrogen activity, apart from a very weak androgen activity; progestogenic activity could not be demonstrated in this species (J. de Visser et al., Arzneim. Forsch. 3.4, 1010, 1984). Although it can be anticipated that the estrogen activity of this compound would prevent its application in breast tumor therapy, it is surprisingly found that this compound has no negative estrogen-like, tumor-increasing effects on DMBA-induced mammary tumors in rats. Contrary to expectation, tumor growth was significantly decreased on treatment with the compound of the invention. This compound can, therefore, be used as a medicament in anti-tumor therapy without having unfavorable side-effects. The term acyl means an acyl group derived from an organic carboxylic acid having 1–18 carbon atoms, such as formic acid, acetic acid, propionic acid, butyric acid, valeric acid, palmitic acid, phenylpropionic acid, maleic acid and citric acid. Preferred acyl groups have 1–6 carbon atoms, and most preferred is the acetyl group.

Compound I is a known compound, the synthesis of which is described e.g. in US patent application Publication No. 3,340,279. Preferably, the crystalline pure monoclinic ($P2_1$) form of (7α,17α)-17-hydroxy-7-methyl -19-nor-17-pregn-5(10)-en-20-yn-3-one (tibolone, compound II) is used, because of its improved stability, bioavailability and shelf-life. The synthesis and use in a pharmaceutical preparation of this monoclinic derivative is disclosed in European Patent Application Publication No. 0,389,035.

The compound of the invention may be administered enterally or parenterally, and for humans in a daily dosage of 0.003–3.0 mg per kg body weight; preferably a daily dosage of 0.03–0.4 mg per kg body weight is administered. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compound may be compressed into solid dosage units, such as pills, tablets, or be processed into capsules or suppositories. By means of pharmaceutically suitable liquids the compound can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general, any pharmaceutically acceptable additive which does not interfere with the function of the active compound can be used.

Suitable carriers with which the compositions can be administered include lactose, starch, cellulose derivatives and the like, or mixtures thereof, used in suitable amounts.

The invention is further illustrated by the following examples.

EXAMPLE 1

A tablet having the following composition was prepared:

| | |
|---|---|
| compound I | 2.5 mg |
| starch | 10 mg |
| ascorbyl palmitate | 0.2 mg |
| magnesium stearate | 0.5 mg |
| lactose | to make up to 100 mg |

Base granules were prepared by mixing the lactose with a portion of the starch. The remainder of the starch was mixed to a slurry with water and added to the mixture. The whole was granulated and dried. These base granules were mixed with ascorbyl palmitate and compound I, sieved, finely mixed with magnesium stearate and then tabletted.

EXAMPLE 2

A tablet having the following composition was prepared:

| | |
|---|---|
| compound II | 2.5 mg |
| starch | 10 mg |
| ascorbyl palmitate | 0.2 mg |
| magnesium stearate | 0.5 mg |
| lactose | to make up to 100 mg |

The preparation of the tablet was performed according to the procedure of Example 1.

EXAMPLE 3

A tablet having the following composition was prepared:

| | |
|---|---|
| (7α,17α)-3,17-dihydroxy-7-methyl-19-nor-17-pregn-5(10)-en-20-yn | 2.5 mg |
| starch | 10 mg |
| ascorbyl palmitate | 0.2 mg |
| magnesium stearate | 0.5 mg |
| lactose | to make up to 100 mg |

The preparation of the tablet was performed according to the procedure of Example 1.

EXAMPLE 4

A tablet having the same composition as in Example 1 was prepared by first mixing compound I with 10% of the lactose and the ascorbyl palmitate and then mixing this mixture with the lactose, starch and starch slurry. The mixture was dried, finely mixed with magnesium stearate and tabletted.

EXAMPLE 5

A tablet having the same composition as in Example 2 was prepared by first mixing compound II with 10% of the lactose and the ascorbyl palmitate and then mixing this mixture with the lactose, starch and starch slurry. The mixture was dried, finely mixed with magnesium stearate and tabletted.

EXAMPLE 6

Four separate experiments were performed (i–iv) with groups of female rats (Sprague-Dawley; age 55–60 days). The number of rats per group was 8. Induction of mammary tumors was performed by two oral administrations of 1 ml of dimethylbenzanthracene (DMBA 10 mg/ml in olive oil) given with 1 week interval.

At an age of 105–115 days when all rats had palpable tumors, the rats were treated orally twice daily with vehicle (control groups) or with compound II (week 0). Because tumors were smaller of volume at the above mentioned age, treatment in experiment iv started when the animals were 115–122 days of age. Compound II was administered orally by gavage as a suspension in 0.5% gelatin and 5% mannitol (w/v) in water (volume: 1 ml/kg). The daily doses of compound II which were administered for 3 weeks, were 2×0.125, 2×0.25, 2×0.5 or 2×1 mg/kg/day. The rats of the control groups were treated orally with vehicle only (0.5% gelatin and 5% mannitol in water), twice daily for 3 weeks. Volume 1 ml/kg.

Before treatment, the rats were palpated weekly for the presence of tumors. After one and two weeks of treatment the tumors were measured weekly under light anesthesia using callipers. The total tumor load per rat represents the sum of the individual areas being the product of the perpendicular diameters. On the last day of treatment the animals were killed under deep anesthesia. At autopsy, blood was collected and plasma was assayed for levels of LH, FSH, estradiol, progesterone, corticosterone, ACTH and prolactin. The tumors were measured as described above, dissected free from connective tissue and weighed.

| | | Results | | | | |
|---|---|---|---|---|---|---|
| | Twice daily dose | Tumor burden (mm$^2$) | | | | Tumor weight |
| Experiment | (mg/kg) | wk 0 | wk 1 | wk 2 | wk 3 | (mg) |
| i. Control | — | 288 | 625 | 1051 | 1743 | 21300 |
| II | 1.0 | 289 | 375 | 422 | 491 | 6130 |
| ii. Control | — | 291 | 534 | 805 | 1070 | 11068 |
| II | 1.0 | 289 | 292 | 343 | 358 | 4800 |
| iii. Control | — | 288 | 620 | 1060 | 1530 | 12700* |
| II | 0.125 | 299 | 620 | 1060 | 1370 | 9300 |
| II | 0.25 | 226 | 490 | 930 | 1190 | 11000* |
| II | 0.5 | 319 | 770 | 900 | 840 | 6500 |
| iv. Control | — | 341 | 800 | 1440 | 2090 | 20700* |
| II | 0.25 | 474 | 760 | 990 | 1290 | 13400 |
| II | 0.5 | 474 | 610 | 890 | 1140 | 11000 |
| II | 1.0 | 323 | 570 | 870 | 1040 | 12000 |

*group of 7 rats

Conclusion: The pregnane derivative of the invention, administered twice daily gives a lower tumor load compared to the control group. A twice daily dose of 1 mg/kg inhibits the tumor growth in rats up to about 70%.

EXAMPLE 7

An experiment was performed with 35 female rats (Sprague-Dawley; age 55–60 days). The rats were divided into 4 groups (number of rats per group: 8–9) according to a randomized block design (3 rats per cage). Induction of mammary tumors was performed by two oral administrations of 1 ml of dimethylbenzanthracene (DMBA 10 mg/ml in olive oil) given with 1 week interval. One group was ovariectomized (OVX-group) and used as reference group.

From the first day of DMBA-treatment, the rats were treated orally with vehicle (control groups and the OVX-group) or with compound II. Compound II was administered orally twice daily by gavage, as a suspension in 0.5% gelatin and 5% mannitol (w/v) in water (volume: 1 ml/kg). The daily doses of compound II which were administered for 10 weeks, were 2×0.25 or 2×1.0 mg/kg/day. The rats of the control and reference groups were treated orally with vehicle only (0.5% gelatin and 5% mannitol in water, volume: 1 ml/kg), twice daily for 10 weeks.

The rats were palpated weekly for the presence of tumors. From week 7 onwards the tumors were measured weekly under light ether anesthesia using callipers.

The total tumor load per rat represents the sum of the individual areas being the product of the two largest perpendicular diameters. On the last day of week 10, the animals were killed under deep anesthesia. The tumors were measured as described above, dissected free from the connective tissue and weighed.

|         | Dose       | Results           |       |       |       |              |
|---------|------------|-------------------|-------|-------|-------|--------------|
|         |            | Tumor burden (mm²) |      |       |       | Tumor weight (mg) |
|         | mg/kg/day  | wk 7  | wk 8  | wk 9  | wk 10 | wk 10        |
| Control |            | 400   | 718   | 1183  | 1761  | 10761        |
| II      | 2 × 0.25   | 10.8  | 14.7  | 125   | 196   | 1161         |
| II      | 2 × 1.0    | 52.4  | 120   | 242   | 322   | 1875         |
| OVX-group |          | 0.0   | 0.0   | 0.0   | 0.0   | 0.0          |

Conclusion: The pregnane derivative of the invention, administered twice daily at a low dose of 0.25 mg/kg, decreases the development of tumors in rats up to about 90%.

EXAMPLE 8

An experiment was performed with 35 female rats (Sprague-Dawley; age 55–60 days). The rats were divided into 4 groups (number of rats per group: 8–9) according to a randomized block design (3 rats per cage). Induction of mammary tumors was performed by two oral administrations of 1 ml of dimethylbenzanthracene (DMBA 10 mg/ml in olive oil) given with 1 week interval. 24 h after the second DMBA-treatment, the rats were treated orally with vehicle (control groups) or with the pregnane derivative of this invention (compound II). The derivative was administered orally twice daily by gavage as a suspension in 0.5% gelatin and 5% mannitol (w/v) in water (Volume: 1 ml/kg). The daily doses of compound II which were administered for 9 weeks, were 2×0.063 or 2 ×0.25 mg/kg/day. The rats of the control and reference groups were treated orally with vehicle only (0.5% gelatin and 5% mannitol in water, volume: 1 ml/kg), twice daily for 9 weeks.

The experiment was further performed according to example 7.

|         | Dose       | Results           |       |       |       |              |
|---------|------------|-------------------|-------|-------|-------|--------------|
|         |            | Tumor burden (mm²) |      |       |       | Tumor weight (mg) |
|         | mg/kg/day  | wk 7  | wk 8  | wk 9  | wk 10 | wk 10        |
| Control |            | 314   | 683   | 1124  | 1544  | 6151         |
| II      | 2 × 0.063  | 261   | 434   | 676   | 957   | 4179         |
| II      | 2 × 0.25   | 107   | 360   | 591   | 825   | 3465         |

Conclusion: The pregnane derivative of the invention, administered twice daily at a low dose of 0.063 mg/kg, decreases the development of tumors in rats up to about 40%.

We claim:

1. A method of inhibiting growth of mammary tumors comprising administering to a mammal a mammary tumor-inhibiting effective amount of a pregnane derivative of the general formula

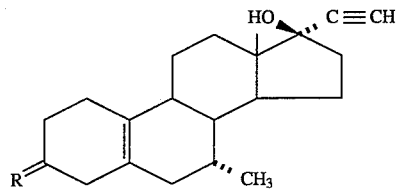

wherein R=$H_2$, (H,OH), (H,OAcyl), or O.

2. The method according to claim 1, wherein R=(H,OH) ((7α,17α) -3, -17-dihydroxy-7-methyl-19-nor-17pregn-5(10) -en-20-yn).

3. The method according to claim 1, wherein R=O ((7α, 17α)-17-hydroxy-7-methyl-19-nor-17-pregn-5(10)-en-20-yn-3-one (compound I)).

4. The method according to claim 3, wherein the pregnane derivative (7α, 17α)-17-hydroxy-7-methyl-19-nor-17-pregn-5(10)-en-20-yn-3-one has the monoclinic $P2_1$ form (compound II).

5. The method according to claim 1, wherein the mammal is a human.

* * * * *